(12) United States Patent
Allwein et al.

(10) Patent No.: US 8,884,014 B2
(45) Date of Patent: Nov. 11, 2014

(54) METHOD FOR PURIFYING A FUSED PYRROLOCARBAZOLE DERIVATIVE

(71) Applicants: Cephalon, Inc., Frazer, PA (US); Cephalon France, Maisons-Alfort (FR)

(72) Inventors: Shawn P. Allwein, Downingtown, PA (US); Arnaud Grandeury, Helfrantzkirch (FR); Guy Piacenza, Creteil (FR); Sebastien Rose, Arsy (FR)

(73) Assignees: Cephalon, Inc., Frazer, PA (US); Teva Sante, La Defense Cedex (Paris) (FR)

(*) Notice: Subject to any disclaimer, the term of this patent is extended or adjusted under 35 U.S.C. 154(b) by 27 days.

(21) Appl. No.: 13/678,886

(22) Filed: Nov. 16, 2012

(65) Prior Publication Data

US 2013/0123499 A1 May 16, 2013

Related U.S. Application Data

(63) Continuation of application No. PCT/US2011/036814, filed on May 17, 2011.

(60) Provisional application No. 61/345,831, filed on May 18, 2010.

(51) Int. Cl.
*C07D 403/00* (2006.01)
*C07D 487/14* (2006.01)

(52) U.S. Cl.
CPC .................................. *C07D 487/14* (2013.01)
USPC .......................................................... 544/331

(58) Field of Classification Search
USPC .......................................................... 544/331
See application file for complete search history.

(56) References Cited

U.S. PATENT DOCUMENTS 7,169,802 B2 * 1/2007 Hudkins et al. ............... 514/410

FOREIGN PATENT DOCUMENTS

WO WO2005/063763 A1 7/2005
WO WO2010/059795 A1 5/2010

OTHER PUBLICATIONS

"Leaving group." Wikipedia. Available at: < http://en.wikipedia.org/wiki/Leaving_group >. Last Updated: Mar. 12, 2013.*
Wikipedia. "Triethylamine." Available at: < http://en.wikipedia.org/wiki/Triethylamine >. Posted: Apr. 15, 2001.*
Leaving Group, Wikipedia, found at p://en.wikipedia.org/wiki/Leaving_group (May 3, 2013).
Triethylamine, Wikipedia, found at http://en.wikipedia.org/wiki/Triethylamine, (c) 2013.

* cited by examiner

*Primary Examiner* — Andrew D Kosar
*Assistant Examiner* — John S Kenyon

(57) ABSTRACT

The present invention relates a method for purifying a fused pyrrolocarbazole compound known as 11-isobutyl-2-methyl-8-(2-pyrimidinylamino)-2,5,6,11,12,13-hexahydro-4Hindazolo[5,4-a]pyrrolo[3,4-c]carbazol-4-one using an acid complex thereof. The present invention also relates to a crystalline form of the acid complex.

7 Claims, 3 Drawing Sheets

X-ray powder diffractogram of form $A_0$ of compound (I)

X-ray powder diffractogram of the acetic acid complex of compound of formula (I)

1H NMR spectrum of the acetic acid complex of the compound of formula (I)

US 8,884,014 B2

METHOD FOR PURIFYING A FUSED PYRROLOCARBAZOLE DERIVATIVE

CROSS REFERENCE TO RELATED APPLICATIONS

This application is a continuation application of International Application No. PCT/US2011/036814, filed May 17, 2011, which claims priority to U.S. Provisional Application Ser. No. 61/345,831, filed May 18, 2010. The disclosures of the aforementioned applications are incorporated herein by reference in their entireties for all purposes.

FIELD OF THE INVENTION

The present invention relates to a method for purifying a pyrrolocarbazole derivative (compound of formula (I) or compound (I)) using an acid complex thereof. The present invention also relates to a crystalline form of an acid complex of formula (Ia).

BACKGROUND OF THE INVENTION

A specific fused pyrrolocarbazole compound known as 11-isobutyl-2-methyl-8-(2-pyrimidinylamino)-2,5,6,11,12,13-hexahydro-4Hindazolo[5,4-a]pyrrolo[3,4-c]carbazol-4-one is a potent, orally-active TIE-2/VEGF-R 40 inhibitor having anti-tumor and anti-angiogenic activity and is represented by the following formula (I):

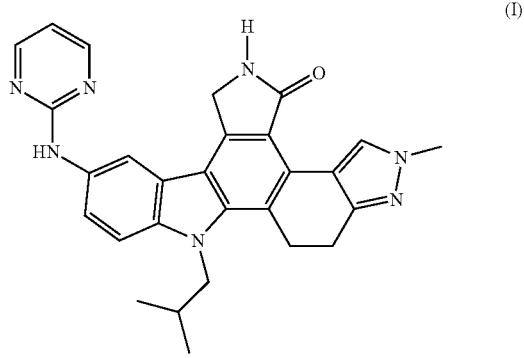 [SMILES: CC(C)Cn1c2ccc(Nc3ncccn3)cc2c2c3c(c4c(c21)CCc1nn(C)cc1-4)C(=O)NC3]

(I)

This compound is herein-referred to as compound (I). U.S. Pat. No. 7,169,802 describes compound I and utility thereof. It notably discloses a method of preparation of this compound according to scheme 1:

Scheme 1

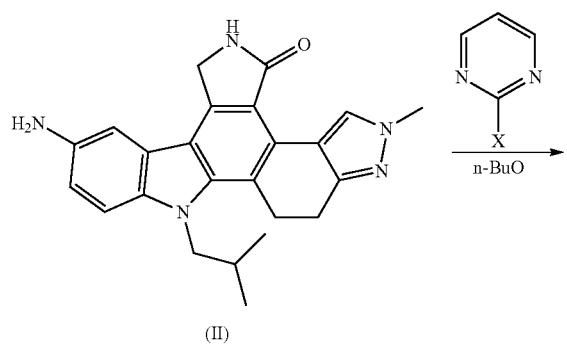

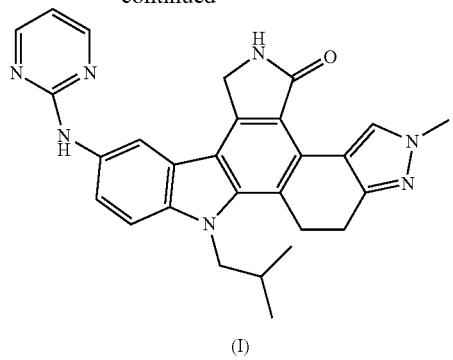

(I)

total yield = 38%

However, the inventors have shown that compound (I) is resulting with poor yields of about 38% and low purity according to such procedure. In particular, it has been shown that the compound of formula (I) thus resulting, contained a high level of the by-product of formula (IV).

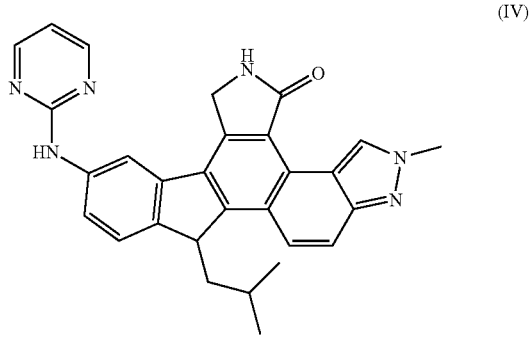 [SMILES: CC(C)CC1c2ccc(Nc3ncccn3)cc2-c2c3c(c4c(ccc5nn(C)cc54)c21)C(=O)NC3]

(IV)

This by-product resulting from the elimination of two hydrogen atoms in the indazolyl moiety of the compound of formula (I) and hence from the aromatization of the ring system, turned out to be particularly difficult to separate from compound of formula (I).

Thus, several purification steps, notably by column chromatography, were required to obtain compound (I) with a pharmaceutically acceptable purity, notably of more than 95%, thus even further lowering the yields.

Therefore, there is a need for an improved process for the manufacture of compound (I) from compound (II) that overcomes the drawbacks of the prior art and, in particular, allows to obtain satisfactory yields and purity.

SUMMARY OF THE INVENTION

The present invention in one aspect provides an acid complex of compound (I). Unexpectedly, the inventors have thus discovered that the crystallization of such a complex allows removing most of the impurities, notably those that are difficult to eliminate by conventional techniques, such as chromatography, and hence to obtain a high purity level.

Thus, the acid complex of the compound (I) according to the invention makes the subsequent purification of compound (I) easier and thus provides a process that is workable on a industrial scale. In particular, it reduces the need of large volumes of solvent generally required for purification by chromatography.

Another object of the present invention is to provide a method for preparing the acid complex of the compound of formula (I) from the compound (II). Advantageously, it has been demonstrated that the use of a base during the nucleophilic substitution step allows increasing the yields of the acid complex and thus of the compound of formula (I), as well as to reduce the resulting impurities. In particular, it has been shown that the presence of a base does not increase the degradation of compound (II).

Another object of the present invention is to provide the use of such an acid complex for purifying compound (I) and notably to reach a purity of more than 95%.

Another object of the present invention is to provide a method for the purification of compound (I), notably comprising the treatment of the acid complex with a decolorizing agent in order to remove the by-product compound of formula (IV).

Still another object of the present invention is to provide a crystalline form of the acid complex of formula (Ia).

These and other objects, features and advantages of the invention will be disclosed in the following detailed description.

DETAILED DESCRIPTION OF THE INVENTION

Figure 1:
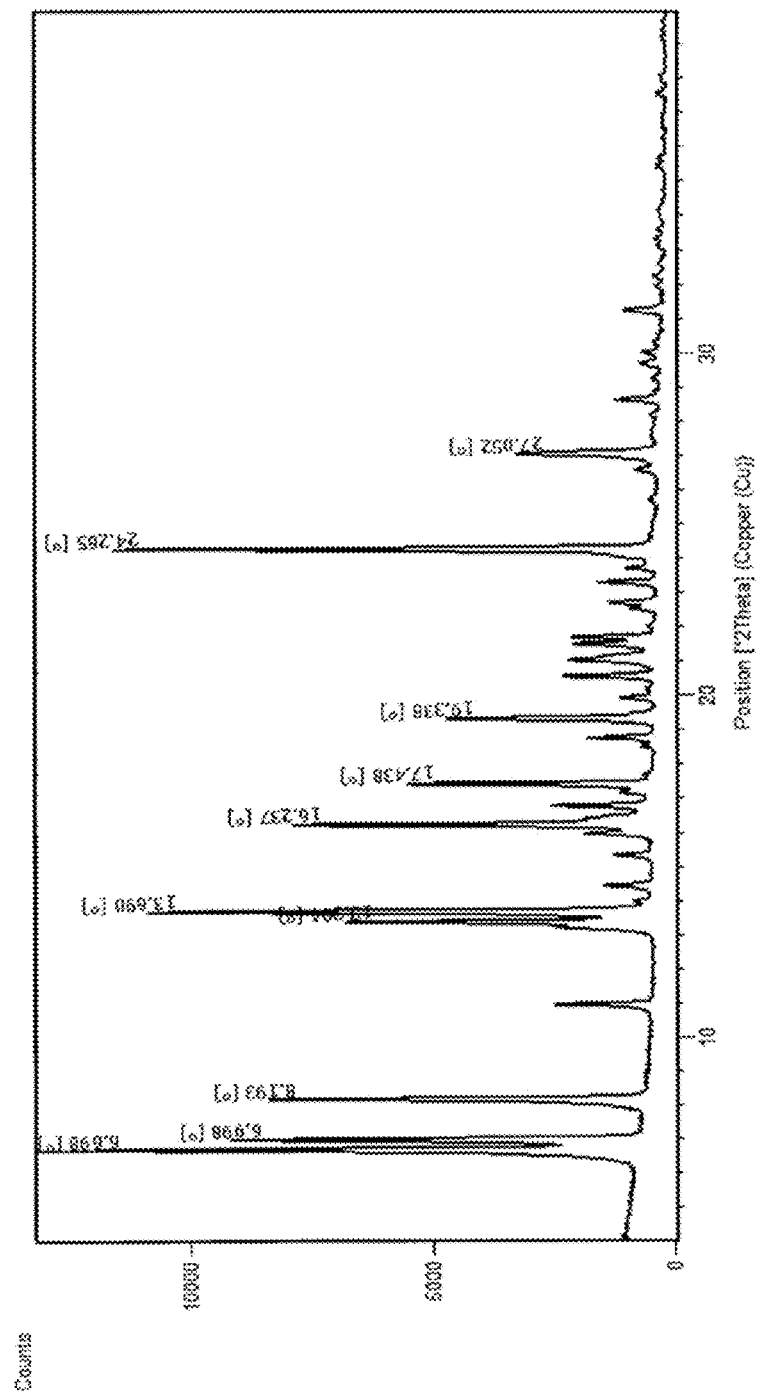
FIG. 1 represents an X-ray powder diffractogram of form $A_0$ of compound (I).

Thus, in one aspect, the invention provides an acid complex of a compound of formula (I):

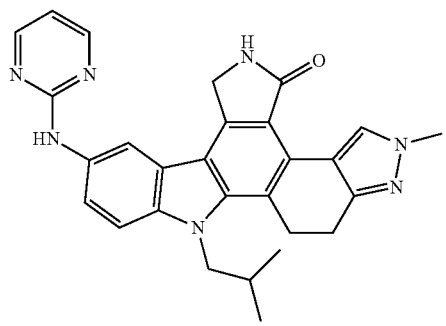

(I)

said acid complex having the following formula (Ia):

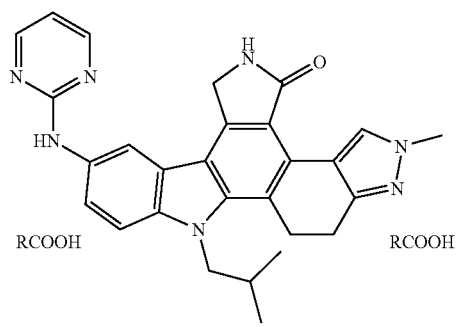

(Ia)

wherein R represents $C_1$-$C_8$ alkyl.

The carboxylic acid RCOOH can be selected in the list consisting of acetic acid, propionic acid, butyric acid, valeric acid, hexanoic acid, heptanoic acid or octanoic acid.

In a particular aspect, RCOOH represents acetic acid. It should be understood that the acetic acid complex of compound I can be referred to as an acid complex of formula (Ia) wherein R represents $C_1$ alkyl.

In a further aspect, R represents $C_2$-$C_8$ alkyl.

In an additional aspect, the invention provides a method for the preparation of the acid complex of formula (Ia), as hereindefined, comprising:

i) contacting a compound of formula (II) with a compound of formula (III) in the presence of a base in a solvent;

(II)

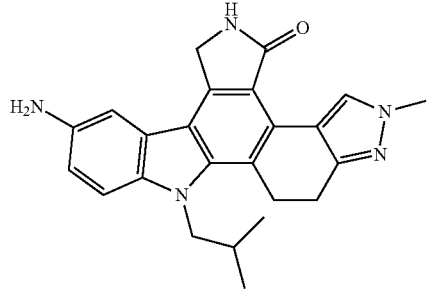

(III)

wherein Hal represents Br, Cl, or I;

ii) contacting the resulting compound of formula (I) with an acid of formula RCOOH; and optionally iii) recovering the resulting acid complex of formula (Ia).

Step i)

In another aspect, the base is an amine, notably a secondary or tertiary amine. In still another aspect, the amine is a trialkylamine. In yet another aspect, the amine is of formula $R_1R_2R_3N$, wherein $R_1$ represents $C_1$-$C_6$ alkyl and $R_2$, $R_3$ are independently selected in the list consisting of H and $C_1$-$C_6$ alkyl. Preferably, the amine is a trialkylamine wherein $R_1$, $R_2$ and $R_3$ independently represent $C_1$-$C_6$ alkyl, notably diisopropylamine or triethylamine; triethylamine being particularly preferred.

Advantageously, it has been shown that the presence of the base enhances the reaction kinetic, while enabling both to increase the yield and the purity of the reaction, notably by reducing the amounts in by-products, in particular those related to the degradation of the compounds of formula (II). Further, it has been observed that the base does not increase the amount of by-product of formula (IV).

In yet a further aspect, the molar ratio of the base relatively to the compound of formula (II) ranges from 1 to 2, and is notably of about 1.5 equivalent.

In still a further aspect, the molar ratio of the compound of formula (III) relative to the compound of formula (II) ranges from 1 to 2, and is notably of about 1.5 equivalent.

There is no particular restriction on the nature of the solvent to be employed, provided that it has no adverse effect on the reaction or on the reagents involved. Examples of suitable solvents include polar solvents, notably alcohols, in particular alcohols having a boiling point above 100° C., such as n-butanol.

The reaction can take place over a wide range of temperatures, and the precise reaction temperature is not critical to the invention. In general, the reaction mixture is heated to reflux, notably at a temperature ranging from 100 to 120° C.

The time required for the reaction may also vary widely, depending on many factors, notably the reaction temperature and the nature of the reagents. While the progress of the reaction can be monitored by HPLC, a period of about 18 to 22 hours is generally sufficient.

Step ii)

According to step ii), the compound of formula (I) is contacted with a carboxylic acid of formula RCOOH. In a preferred embodiment, the carboxylic acid is added to the reaction mixture resulting at the end of step i).

Preferably, the volume of RCOOH that is added to the reaction mixture ranges from 1 to 20 volumes, notably from 5 to 15 volumes, relative to the compound of formula (II) or (I).

The temperature of addition of the acid RCOOH to the reaction mixture is not critical. It can be chosen notably between the boiling point and the melting point of the acid RCOOH, and in particular in the range of 60 to 120° C. Preferably, the reaction mixture of step i) is cooled to about 75° C., before the acid RCOOH is added.

The reaction mixture is then generally heated to a temperature ranging from 60° C. to 80° C., notably at 75° C., over a period of about 10 to 30 minutes.

Step iii)

In an additional aspect, the acid complex of formula (Ia) is recovered from the reaction mixture.

In a particular embodiment, step iii) comprises:
a) crystallizing the resulting acid complex of formula (Ia); and
b) recovering the crystallized complex of formula (Ia).

The complex of formula (Ia) form can be crystallized from the reaction mixture by conventional methods, including notably cooling or chilling, crystal seeding, evaporation of a portion of the solution, or precipitation by adding an antisolvent such as methyl tert-butyl ether (MTBE).

A preferred embodiment comprises cooling the reaction mixture to about 20° C. In particular, the reaction mixture can be cooled rapidly by standard cooling methods, typically with a temperature cooling rate in the range of −0.1° C./min to −10° C./min.

The crystallized complex of formula (Ia) can be isolated by any conventional methods including filtration and centrifugation. The recovered crystals of the acid complex may then be washed with a solvent, for instance with methyl tert-butyl ether (MTBE).

In an additional aspect, the invention provides a crystalline form of an acid complex of formula (Ia):

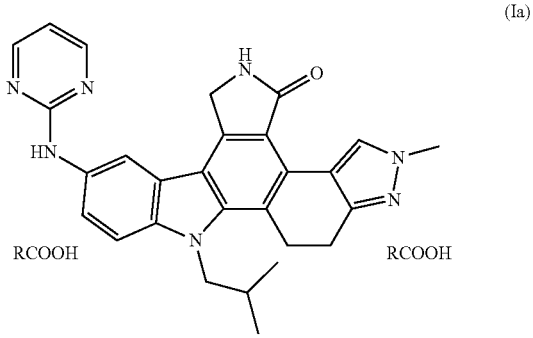

Figure 2:
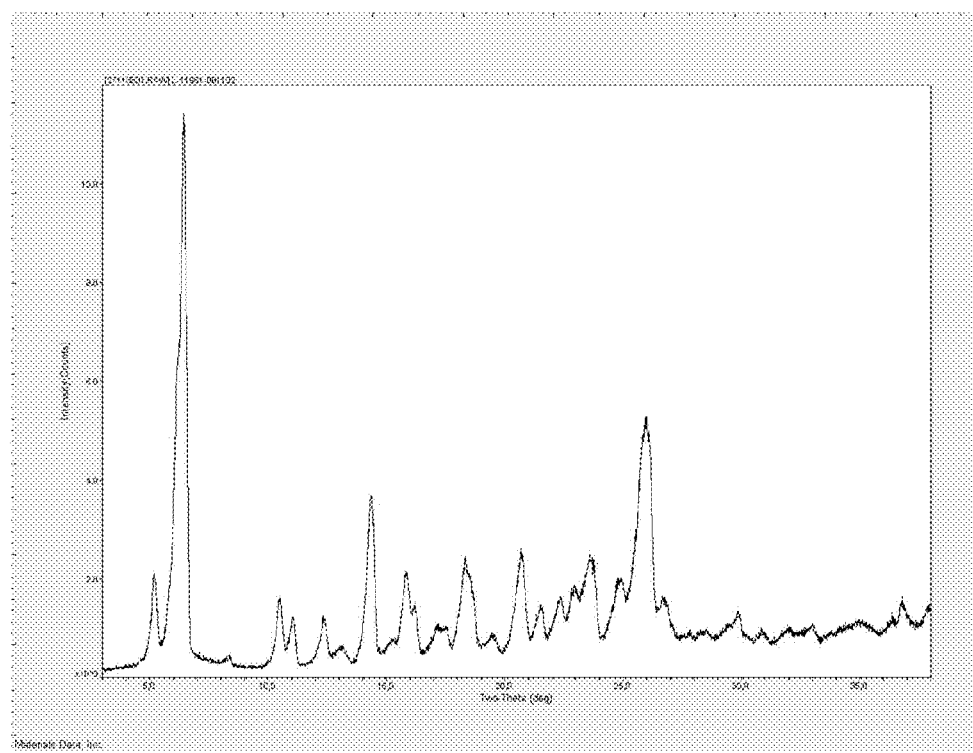
FIG. 2 represents the X-ray powder diffractogram of the acetic acid complex of compound of formula (I).

(Ia)

wherein R represents $C_1$ alkyl, characterized by an X-ray powder diffractogram comprising one or more of the following peaks: 5.19±0.2 degrees 2-Theta; 6.17±0.2 degrees 2-Theta; 6.44±0.2 degrees 2-Theta; 14.36±0.2 degrees 2-Theta; and 26.09±0.2 degrees 2-Theta, when measured using Cu-Kα radiation. In one aspect, the X-ray powder diffractogram comprises a peak at 6.44±0.2 degrees 2-Theta and one or more of the following peaks: 5.19±0.2 degrees 2-Theta; 6.17±0.2 degrees 2-Theta; 14.36±0.2 degrees 2-Theta; and 26.09±0.2 degrees 2-Theta, when measured using Cu-Kα radiation. In another aspect, the X-ray powder diffractogram comprises peaks at 6.44±0.2 degrees 2-Theta and 6.17±0.2 degrees 2-Theta and one or more of the following peaks: 5.19±0.2 degrees 2-Theta; 14.36±0.2 degrees 2-Theta; and 26.09±0.2 degrees 2-Theta, when measured using Cu-Kα radiation. In a further aspect, the X-ray powder diffractogram comprises peaks at 6.44±0.2 degrees 2-Theta; 6.17±0.2 degrees 2-Theta; and 26.09±0.2 degrees 2-Theta and one or more of the following peaks: 5.19±0.2 degrees 2-Theta and 14.36±0.2 degrees 2-Theta, when measured using Cu-Kα radiation. In a still further aspect, the X-ray powder diffractogram comprises peaks at 5.19±0.2 degrees 2-Theta; 6.17±0.2 degrees 2-Theta; 6.44±0.2 degrees 2-Theta; 14.36±0.2 degrees 2-Theta; and 26.09±0.2 degrees 2-Theta, and one or more of the following peaks: 10.51±0.2 degrees 2-Theta; 15.84±0.2 degrees 2-Theta; 18.33±0.2 degrees 2-Theta; 20.69±0.2 degrees 2-Theta; and 23.71±0.2 degrees 2-Theta, when measured using Cu-Kα radiation. In a yet further aspect, the crystalline acetic acid complex of formula (Ia) has an X-ray powder diffractogram substantially as depicted in FIG. 2.

In a preferred embodiment, the crystalline form of an acid complex of formula (Ia) where R represents $C_1$ alkyl has a purity of at least about 92%. In a more preferred embodiment, the crystalline form of an acid complex of formula (Ia) where R represents $C_1$ alkyl has a purity of at least about 97%. In a still more preferred embodiment, the crystalline form of an acid complex of formula (Ia) where R represents $C_1$ alkyl has a purity of at least about 99.5%.

Advantageously, it has been shown that the crystallization of the complex of formula (Ia) allows to eliminate most of the impurities resulting from the preparation steps of compound of formula (I). Thus, after crystallization, the resulting complex is generally recovered in a purity ranging from 92 to 99.5% or more. In particular, removing the majority of the impurities generally allows a purity ranging from 92 to 97%. The remaining impurities are mainly by-product of formula (IV) that tends to crystallize together with the acid complex of formula (I). Further removing compound of formula (IV) hence allows a purity equal or greater than 99.5%.

In an additional aspect, the invention provides an acid complex of formula (Ia) obtainable according to the method herein-disclosed.

In still an additional aspect, the invention provides the use of an acid complex of formula (Ia) for purifying or in a method for purifying the corresponding compound of formula (I) or a pharmaceutically acceptable salt thereof.

In a preferred embodiment, the purified compound of formula (I) has a purity of more than 98%, preferably of more than 99%.

In an additional aspect, the invention provides a method for the purification of the compound of formula (I) as herein-defined, comprising:
i) converting the acid complex of formula (Ia) as herein-defined into the corresponding compound of formula (I);
ii) contacting the resulting compound of formula (I) with a decolorizing agent; and optionally
iii) recovering the purified compound of formula (I).

In yet another aspect, the step of converting the acid complex of formula (Ia) into the compound of formula (I) is carried out by drying the complex at a temperature comprised in the range of from 70° C. to 90° C., notably at a temperature of about 80° C.

Alternatively, the step of converting the acid complex of formula (Ia) into the compound of formula (I) can be carried out by dissolving in a solvent the complex of formula (Ia), notably in a solvent suitable for crystallizing the compound of formula (I), for example under the polymorphic form $A_0$. Polymorphic form $A_0$ of compound (I) has been disclosed in international patent application n° PCT/US2009/065099, the content of which is herein-incorporated by reference.

FIG. 1 represents an X-ray powder diffractogram of form $A_0$ of compound (I). It presents representative peaks according to Table 1.

TABLE 1

| Peak No. | Angle [°2 Theta] | d-spacing [Angstrom] | Intensity [%] |
|---|---|---|---|
| 1 | 6.70 | 13.19 | 100 |
| 2 | 7.00 | 12.62 | 67 |
| 3 | 8.19 | 10.78 | 63 |
| 4 | 10.97 | 8.06 | 16 |
| 5 | 13.22 | 6.69 | 15 |
| 6 | 13.39 | 6.61 | 51 |
| 7 | 13.69 | 6.46 | 84 |
| 8 | 14.45 | 6.12 | 8 |
| 9 | 15.35 | 5.77 | 6 |
| 10 | 15.98 | 5.54 | 11 |
| 11 | 16.24 | 5.45 | 59 |
| 12 | 16.80 | 5.27 | 16 |
| 13 | 17.19 | 5.15 | 5 |
| 14 | 17.44 | 5.08 | 41 |
| 15 | 18.79 | 4.72 | 11 |
| 16 | 19.34 | 4.59 | 35 |
| 17 | 19.94 | 4.45 | 5 |
| 18 | 20.57 | 4.31 | 15 |
| 19 | 21.04 | 4.22 | 13 |
| 20 | 21.19 | 4.19 | 7 |
| 21 | 21.51 | 4.13 | 13 |
| 22 | 21.72 | 4.09 | 13 |
| 23 | 22.72 | 3.91 | 8 |
| 24 | 23.30 | 3.82 | 10 |
| 25 | 23.72 | 3.75 | 5 |
| 26 | 24.26 | 3.67 | 91 |
| 27 | 27.05 | 3.29 | 23 |
| 28 | 28.64 | 3.11 | 7 |
| 29 | 31.26 | 2.86 | 6 |

Suitable solvents for crystallizing the compound of formula (I) under the polymorphic form $A_0$ may notably be selected in the list consisting of 1-butanol; 1-pentanol; 1-propanol; 2-butanol; 2-butanone; 2-pentanone; 3-pentanone; acetone; acetonitrile; butyronitrile; chlorobenzene; cyclohexane; dichloromethane; di-isopropyl-amine; dimethyl-sulfoxide; EGDE; ethanol; ethyl acetate; ethylene glycol; heptane; iPrOH; isopropyl acetate; methanol; methyl acetate; methyl ethyl ketone; methyl isopropyl ketone; methyl tert-butyl ether; n-butyl-acetate; pentanol; propanitrile; pyridine; sec-butanol; tetrahydrofuran; tetrahydropyrane; toluene; triethylamine; water; xylene; and mixtures thereof, including 6:4 N-methylpyrrolidone; water; 1:1 N-methylpyrrolidone:water; 9:1 1-2 dichloromethane; N-methylpyrrolidone; 7:3 1-2 dichloromethane; isopropyl acetate.

The dissolution of the complex can be performed at a temperature in the range of 60° C. and 80° C., notably of about 70° C., under stirring.

The progress of the reaction of conversion of the acid complex into the compound of formula (I) can be monitored by RX diffraction. Thus, the conversion reaction can be performed over a period sufficient to convert the whole acid complex of formula (Ia) into the compound of formula (I).

In a preferred embodiment, the resulting compound of formula (I) is recovered from the reaction mixture prior the step of treatment with the decolorizing agent, notably by crystallizing the compound of formula (I) and isolating the crystals.

Crystallization can be performed by any conventional methods, including notably cooling or chilling, crystal seeding, evaporation of a portion of the solution, or precipitation by adding an anti-solvent.

A preferred embodiment comprises cooling the reaction mixture to about 10° C., notably rapidly by standard cooling methods, typically with a cooling rate temperature in the range of −0.1 to −10° C./min.

The crystallized compound of formula (I) can be isolated by any conventional methods including filtration and centrifugation. The recovered crystals of the compound of formula (I) may then be washed with a solvent, for instance with isopropyl acetate. The isolated product may then be dried under vacuum.

In a particular aspect, the step of contacting the compound of formula (I) with a decolorizing agent is carried out in a solvent selected in the list consisting of dichloromethane, methanol, ethanol or any solvent capable to solubilise compound (I) or any binary or ternary mixture thereof.

In yet a further aspect, the decolorizing agent is an activated charcoal, notably a steam or chemically activated charcoal. Examples of suitable activated charcoals are those provided under the trade names LSM™, L3S™, 3S™, DARCO G60™ for steam activated charcoals and CPL™, ENO PC™, CAP SUPER™ for chemically activated charcoals; typically from Ceca or Norit manufacturers. Preferred charcoal is ENO PC™ charcoal.

Advantageously, it has been shown that the decolorizing agent allows substantially removing by adsorption, any residual by-products which can be present in the reaction mixture together with the compound of formula (I) (or with the acid complex of formula (Ia) respectively), in particular the by-product of formula (IV).

The purified compound of formula (I) may then be recovered by filtering the reaction mixture, and evaporating the solvent under vacuum.

The recovered compound of formula (I) may then be optionally recrystallized, notably under polymorphic form $A_0$. In a certain aspect, the compound of formula (I) can be dissolved in isopropylacetate and then cooled to a temperature of about 10° C. to 20° C. until complete formation of polymorphic form $A_0$.

The crystals of the purified compound of formula (I) may then be recovered by any conventional methods, notably by centrifugation, and washed with a solvent such as isopropylacetate.

In another aspect, the invention provides a method for the purification of the compound of formula (I) as herein-defined, said method comprising the steps of:
  i) contacting the acid complex of formula (Ia) as herein-defined with a decolorizing agent in a solvent;
  ii) converting the resulting acid complex of formula (Ia), into the corresponding compound of formula (I); and optionally
  iii) recovering the purified compound of formula (I).

The steps of treatment with a decolorizing agent (step i) and of conversion of the acid complex of formula (Ia) into the compound of formula (I) (step ii) can be performed according to the same procedures than those herein-disclosed.

In a still further aspect, the resulting purified compound of formula (I) is further reacted with an acid so as to obtain an acid addition salt, preferably a monoacid addition salt.

In another aspect, the acid is the paratoluenesulfonic acid (PTSA).

The following terms and expressions used herein-have the indicated meanings.

As used herein, the term "about" refers to a range of values from ±10% of a specified value. For example, the phrase "about 50 mg" includes ±10% of 50, or from 45 to 55 mg.

The term "complex", as used herein, refers to the non covalently bounded association of two molecules of the acid RCOOH with one molecule of the compound of formula (I).

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. Lower alkyl groups, which are preferred, are alkyl groups as defined above which contain 1 to 4 carbons. A designation such as "C1-C4 alkyl" refers to an alkyl radical containing from 1 to 4 carbon atoms.

The term "solvent," as used herein, means a substance, typically a liquid, that is capable of completely or partially dissolving another substance, typically a solid, and which is nonreactive towards the starting reagents, the intermediates or the products, at the reaction temperature considered, it being possible for the latter to vary from the solidification point of the solvent to the boiling point of the solvent.

The term "anti-solvent," as used herein, means a solvent in which a compound is substantially insoluble.

As used herein, the term "decolorizing agent" refers to a porous or finely divided carbon, notably activated, with a large surface area, that can adsorb coloured impurities from the liquid reaction mixture, notably aromatic impurities.

As used herein, the term "volume" or "V", when referring to a ratio, means a (liter/kilogramme) (L/kg) ratio.

EXAMPLES

Other features of the invention will become apparent in the course of the following descriptions of exemplary embodiments. These examples are given for illustration of the invention and are not intended to be limiting thereof.

Material and Methods

Compound (II) is supplied by Cephalon (typical purity>92% LCAP); it can be prepared according to the preparation of example I-29 of WO-2005/063763.

Triethylamine was purchased from SAFC (typical purity>99%). 2-BromoPyrimidine was purchased from Acros (typical purity>98%). Solvents were purchased from SDS Carlo Erba (typical purity: PPS grade)

HPLC

A reversed-phase HPLC method was developed and qualified for determining the identity, the assay and purity of compound of formula (I) drug substance. The analysis is performed on an XTerra MS C18 column (150×4.6 mm, 5 μm packing) using a 55-85% organic gradient over 27 minutes, and measuring the absorbance at 270 nm.

Analysis Parameters
Column: Xterra MS C18, 150×4.6 mm, 5μ
Column temperature: 30° C.
Injection volume: 10 μL
Detection: UV, 270 nm
Flow rate: 1.0 mL/min
Run time: 27 minutes
Mobile phase A: 10 mM aqueous ammonium acetate
Mobile phase B: 10 mM ammonium acetate in 50:50 acetonitrile/methanol
Gradient:

| Time (min) | % A | % B |
|---|---|---|
| 0.0 | 45 | 55 |
| 7.0 | 40 | 60 |
| 11.0 | 40 | 60 |
| 23.0 | 15 | 85 |
| 23.1 | 45 | 55 |
| 27.0 | 45 | 55 |

X-Ray Powder Diffraction (XRPD)

The X-ray powder diffraction (XRPD) pattern for the acetic acid complex of compound of formula (I) was resulting using a Rigaku Miniflex II diffractometer using Cu Kα radiation.

FIG. 2 represents the X-ray powder diffractogram of the acetic acid complex of compound of formula (I). It presents representative XRPD peaks according to Table 2.

TABLE 2

XRPD peaks of the crystallized acetic acid complex of formula (Ia)

| Peak n° | Angle (2-Theta) | d-spacing (Å) | Intensity I (%) |
|---|---|---|---|
| 1 | 5.19 | 17.01 | 17.5 |
| 2 | 6.17 | 14.31 | 53.3 |
| 3 | 6.44 | 13.71 | 100.0 |
| 4 | 8.38 | 10.54 | 1.7 |
| 5 | 10.51 | 8.41 | 13.0 |
| 6 | 11.03 | 8.01 | 8.6 |
| 7 | 12.34 | 7.17 | 8.1 |
| 8 | 13.19 | 6.71 | 2.0 |
| 9 | 14.36 | 6.16 | 29.7 |
| 10 | 15.20 | 5.82 | 1.2 |
| 11 | 15.84 | 5.59 | 14.9 |
| 12 | 16.19 | 5.47 | 8.5 |
| 13 | 17.19 | 5.15 | 4.8 |
| 14 | 17.51 | 5.06 | 4.1 |
| 15 | 18.33 | 4.84 | 16.7 |
| 16 | 19.51 | 4.55 | 2.8 |
| 17 | 20.69 | 4.29 | 17.2 |
| 18 | 21.51 | 4.13 | 5.9 |
| 19 | 22.39 | 3.97 | 5.1 |
| 20 | 22.98 | 3.87 | 8.5 |
| 21 | 23.71 | 3.75 | 13.1 |
| 22 | 24.89 | 3.57 | 5.4 |
| 23 | 26.09 | 3.41 | 33.8 |
| 24 | 26.73 | 3.33 | 4.0 |
| 25 | 27.84 | 3.21 | 1.5 |
| 26 | 28.28 | 3.15 | 1.5 |
| 27 | 28.55 | 3.12 | 1.6 |
| 28 | 29.52 | 3.02 | 2.9 |
| 29 | 29.85 | 2.99 | 5.5 |
| 30 | 30.87 | 2.89 | 2.5 |
| 31 | 32.06 | 2.79 | 1.6 |
| 32 | 33.02 | 2.71 | 2.5 |
| 33 | 33.80 | 2.65 | 1.0 |
| 34 | 34.13 | 2.62 | 1.0 |
| 35 | 34.84 | 2.57 | 2.7 |
| 36 | 35.21 | 2.55 | 2.1 |
| 37 | 36.38 | 2.47 | 3.4 |
| 38 | 36.81 | 2.44 | 5.9 |

Nuclear Magnetic Resonance (NMR)

The NMR spectra were acquired on a Bruker Avance AV-400 spectrometer operating at 400 MHz for $^1$H spectra and 100 MHz for $^{13}$C spectra using CDCl$_3$ as the solvent.

Figure 3:
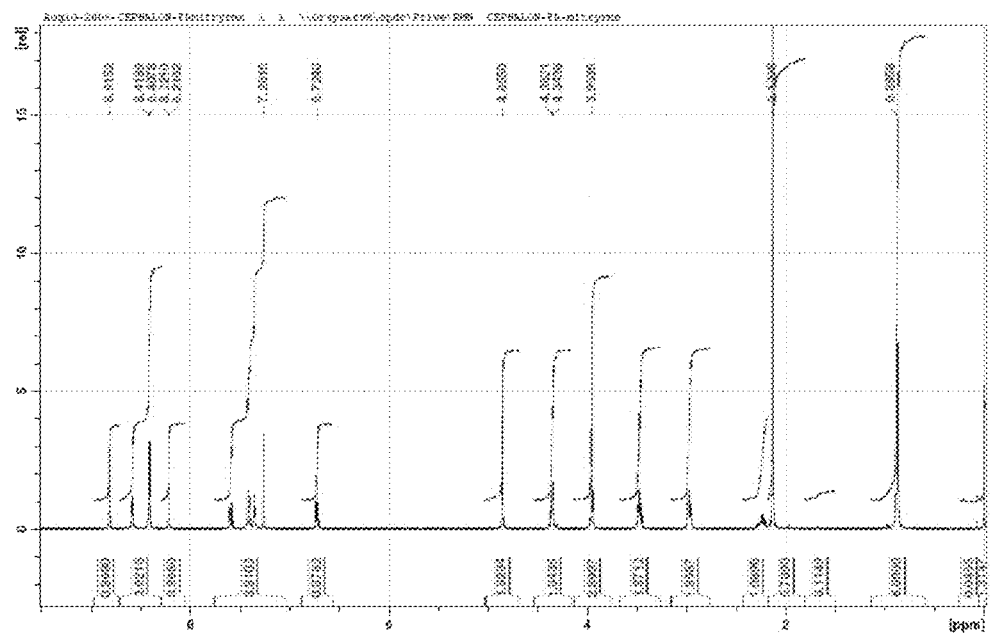
FIG. 3 represents the $^1H$ NMR spectrum of the acetic acid complex of the compound of formula (I).

FIG. 3 represents the $^1$H NMR spectrum of the acetic acid complex of the compound of formula (I). It presents representative peaks according to table 3. Peaks at 0.88 (corresponding to the compound (I)) and at 2.13 (corresponding to acetic acid) confirm the presence of two molecules of acetic acid for one molecule of compound of formula (I).

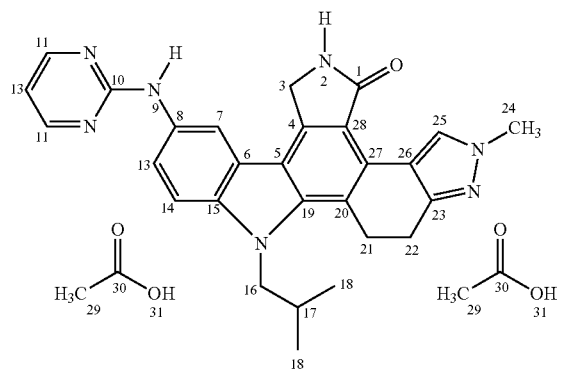

TABLE 3

| Position | Group | 1H δ/TMS (ppm) | 13C δ/TMS (ppm) |
|---|---|---|---|
| 1 | C | — | 174.03 |
| 2 | NH | 8.58 | — |
| 3 | CH2 | 4.86 | 44.64 |
| 4 | C | — | 117.68 |
| 5 | C | — | 116.78 |
| 6 | C | — | 118.29 |
| 7 | CH | 8.22 | 112.73 |
| 8 | C | — | 149.76 |
| 9 | NH | — | — |
| 10 | C | — | 160.25 |
| 11 | CH | 8.41 | 157.93 |
| 12 | CH | 6.72 | 111.75 |
| 13 | CH | 7.59 | 119.81 |
| 14 | CH | 7.41 | 110.51 |
| 15 | C | — | 138.87 |
| 16 | CH2 | 4.35 | 53.21 |
| 17 | CH | 2.22 | 30.31 |
| 18 | CH3 | 0.88 | 20.21 |
| 19 | C | — | 139.77 |
| 20 | C | — | 122.07 |
| 21 | CH2 | 2.98 | 21.00 |
| 22 | CH2 | 3.48 | 25.68 |
| 23 | C | — | 141.77 |
| 24 | CH3 | 3.95 | 38.77 |
| 25 | CH | 8.82 | 132.41 |
| 26 | C | — | 127.47 |
| 27 | C | — | 114.38 |
| 28 | C | — | 138.87 |
| 29 | CH3 | 2.13 | 21.56 |
| 30 | C=O | — | 175.87 |
| 31 | OH | — | — |

Example 1

Preparation of the Acetic Acid Complex of Formula (Ia)

A reactor was charged at about 20° C. with the compound of formula (II) (12.99 kg; 1 eq) and butanol-1 (130 L; 10 V). The mixture was stirred (80 rpm) at 20° C. for 5 minutes. Triethylamine (6.82 L; 1.5 eq.) and 2-bromo pyrimidine (7.79 kg; 1.5 eq) were added at 20° C. Then the reaction mixture stirred at 100 rpm was heated to reflux (TM=117° C.) at least 20 h (checking that the reaction was complete by HPLC, if it is necessary, continue the reflux). After cooling the mixture to 60° C., acetic acid (195 L) was added. The mixture was heated to 75° C. (disappearance of solid particles) and stirred for 15 minutes. Then, the mixture was cooled to 20° C. (−0.3° C./min) and was stirred for 2 hours. The precipitated solids were isolated by centrifugation and washed with Methyl tert-Butyl Ether (MTBE). The product was dried under vacuum at 40° C. to yield 17.9 kg of the acetic acid complex of formula (Ia) with a yield of 92% and a purity of 96.5%.

Example 2

Converting the Acetic Acid Complex into the Compound of Formula (I) Via a Polymorphic Transformation A reactor was charged at about 20° C. with the acetic acid complex of example 1 (9.02 kg; 1 eq) and isopropyl acetate (390 L; 40V). The mixture was stirred (80 rpm) at 20° C. for 15 minutes. After heating to 70° C., the mixture was stirred at 80 rpm until complete formation of polymorphic form $A_0$ (checking that the reaction was complete by RX). Then the reaction mixture was cooled to 10° C. and was stirred for at least 2 hours. The precipitated solids were isolated by centrifugation and washed with isopropyl acetate. The product was dried under vacuum at 40° C. to yield 6.11 kg of crude compound (I) as form $A_0$ (yield=85.6%)

Example 3

Charcoal Treatment and Polymorphic Transformation into Purified Compound of Formula (I)

A reactor was charged at about 20° C. with crude the compound of formula (I) form $A_0$ (4.040 kg; 1 eq, dichloromethane (222 L; 40V) and ethanol (56 L; 10 V). The mixture was stirred yield (80 rpm) at 20° C. for 15 minutes in order to obtain a solution perfectly clear. The mixture was purified with 50% w/w activated charcoal lens (2×1 kg; 49.5% w/w). Then the liquors were filtered through a 0.3 μm Cuno filter cartridge to remove insoluble particles (activated charcoal). The solvents were evaporated until dryness under vacuum. Isopropyl acetate (265 L; 58 V) was added to the mixture and 50 L of azeotropic mixture was evaporated under vacuum. After cooling the mixture to 20° C., the mixture was stirred at 80 rpm until complete formation of polymorphic form $A_0$ (checking that the reaction was complete by RX/DSC, if it is necessary, heat to 70° C.). Then the reaction mixture was cooled to 10° C. The precipitated solids were isolated by centrifugation and washed with isopropyl acetate. The product was dried under vacuum at 40° C. to yield the compound (I) under form $A_0$ (3.280 kg; yield=81.19%; purity=99.2%).

Example 4

Preparation of the Acid Addition Salt of the Compound of Formula (I) with PTSA (Monotosylate)

A reactor was charged at about 20° C. with the compound of formula (I) form $A_0$ (6.075 kg; 1 eq) and dichloromethane (92 L; 15 V). The mixture was stirred (80 rpm) at 20° C. for 15 minutes. After cooling the mixture to 10° C., paratoluene sulfonic acid (PTSA—2.417 kg; 1 eq) was added portion wise. The mixture was stirred at 80 rpm at 10° C. for 1 hour. Then, MTBE (122 L; 15 V) was added portion wise via a feed vessel. The mixture was heated to 45° C. at least 1 h (checking that the reaction was complete by RX/DSC, if it is necessary, continue the contact). After cooling the mixture to 10° C., the precipitated solids were isolated by filtration and washed with MTBE. The product was dried under vacuum at 40° C. to yield the addition salt of compound of formula (I) with PTSA (8.045 kg; yield=97.3%; purity=99.1%).

Example 5

Preparation of the Compound of Formula (I) Free Base of Formula (I) from Compound of Formula (II)

A reactor was charged at about 20° C. with the compound of formula (II) (1 eq) and butanol-1 (10 V). The mixture was stirred (80 rpm) at 20° C. for 5 minutes. Triethylamine (1.4 eq.) and 2-bromo pyrimidine (1.4 eq) were added at 20° C. Then the reaction mixture stirred at 100 rpm was heated to reflux (TM=117° C.) at least 20 h (checking that the reaction was complete by HPLC, if it is necessary, continue the reflux). After cooling the mixture to 75° C., acetic acid (5V) was added. The mixture was stirred at 75° C. until the disappearance of solid particles. Then, the mixture was cooled to 20° C. (—0.3° C./min). The precipitated solids (wet compound (I)/ acetic acid complex of formula (Ia)) were isolated by centrifugation and washed with methyl-tert-butyl-ether (MTBE). The product was dried under vacuum at 80° C. to yield compound (I) as its free base of formula (I).

The invention claimed is:

1. A crystalline acid complex of formula (Ia):

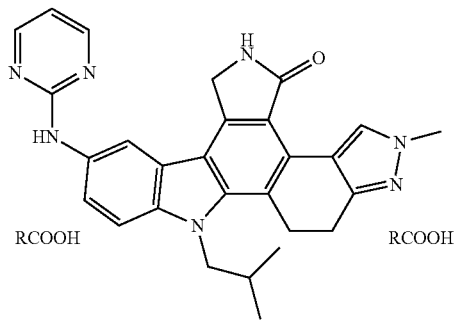

(Ia)

wherein R represents methyl, characterized by an X-ray powder diffractogram comprising one or more of the following peaks: 5.19±0.2 degrees 2-Theta; 6.17±0.2 degrees 2-Theta; 6.44±0.2 degrees 2-Theta; 14.36±0.2 degrees 2-Theta; and 26.09±0.2 degrees 2-Theta.

2. A method for preparing the crystalline acid complex of formula (Ia) of claim 1 comprising:

i) contacting a compound of formula (I) with acetic acid

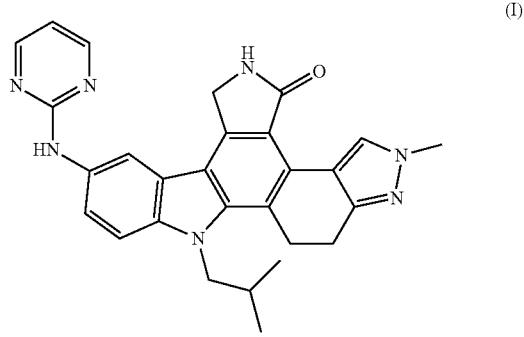 [SMILES: CC(C)Cn1c2ccc(Nc3ncccn3)cc2c2c3c(c4c(c21)CCc1nn(C)cc1-4)C(=O)NC3]

(I)

to form an acid complex of Formula (Ia); and ii) crystallizing the resulting acid complex of Formula (Ia).

3. The method according to claim 2 optionally comprising contacting the acid complex of Formula (Ia) with a decolorizing agent.

4. The method according to claim 2 or 3 optionally comprising recovering the crystallized complex of formula (Ia).

5. The method according to claim 3 where in the decolorizing agent is a steam or chemically activated charcoal.

6. The method of claim 4 wherein the recovered crystalline complex of Formula (Ia) is at least about 92% pure.

7. The method of claim 4 wherein the recovered crystalline complex of Formula (Ia) is at least about 97% pure.

* * * * *